US00RE46612E

(19) United States
(12) Reissued Patent
Bernstein

(10) Patent Number: US RE46,612 E
(45) Date of Reissued Patent: Nov. 21, 2017

(54) SCENT SAMPLER AND AIR FRESHENER

(71) Applicant: Scentisphere LLC, Carmel, NY (US)

(72) Inventor: Robert Bernstein, White Plains, NY (US)

(73) Assignee: Scentisphere, LLC, Carmel, NY (US)

(21) Appl. No.: 15/188,017

(22) Filed: Jun. 21, 2016

Related U.S. Patent Documents

Reissue of:
(64) Patent No.: 8,777,127
Issued: Jul. 15, 2014
Appl. No.: 12/972,979
Filed: Dec. 20, 2010

U.S. Applications:
(60) Provisional application No. 61/288,472, filed on Dec. 21, 2009.

(51) Int. Cl.

| | |
|---|---|
| ***B65D 1/32*** | (2006.01) |
| ***B32B 37/20*** | (2006.01) |
| ***B32B 7/12*** | (2006.01) |
| ***B32B 27/32*** | (2006.01) |
| ***B32B 27/36*** | (2006.01) |
| ***A61L 9/04*** | (2006.01) |
| ***A61L 9/12*** | (2006.01) |
| *B31B 120/00* | (2017.01) |
| *B32B 37/12* | (2006.01) |
| *B32B 38/00* | (2006.01) |
| *B32B 37/24* | (2006.01) |

(Continued)

(52) U.S. Cl.
CPC ..... *B32B 37/203* (2013.01); *A61L 9/042* (2013.01); *A61L 9/12* (2013.01); *B32B 7/12* (2013.01); *B32B 27/32* (2013.01); *B32B 27/36* (2013.01); *B31B 50/81* (2017.08); *B31B 2100/00* (2017.08); *B31B 2120/00* (2017.08); *B32B 37/12* (2013.01); *B32B 38/145* (2013.01); *B32B 2037/243* (2013.01); *B32B 2038/042* (2013.01); *B32B 2038/047* (2013.01); *B32B 2038/166* (2013.01); *B32B 2317/12* (2013.01); *B32B 2323/10* (2013.01); *B32B 2367/00* (2013.01); *B32B 2509/00* (2013.01); *Y10T 156/1036* (2015.01)

(58) Field of Classification Search
CPC ..... A45D 34/00; A44C 15/002
USPC .... 239/56, 326–328, 44; 222/633, 103, 105, 222/212, 213, 215, 192
See application file for complete search history.

(56) References Cited

U.S. PATENT DOCUMENTS 3,412,907 A * 11/1968 Faso ..... A45D 34/02 222/187
3,806,474 A * 4/1974 Blair ..... C08G 18/10 521/116

(Continued)

*Primary Examiner* — Cary Wehner
(74) *Attorney, Agent, or Firm* — Levine Mandelbaum PLLC

(57) ABSTRACT

A scent sampler and air freshener has a wafer of an absorbent resilient material infused with a liquid containing a scent. The wafer is encapsulated in a chamber formed between two panels of sheet material with edges sealed together to form an envelope. An opening in one of the panels enables scent from the liquid to be emitted to the ambient atmosphere. The rate of emission can be increased by squeezing the panels to compress the wafer. The interior surfaces of the panels can be coated with a barrier film to prevent leakage of the liquid from contaminating the sheet material.

14 Claims, 11 Drawing Sheets

(51) Int. Cl.

| | |
|---|---|
| *B32B 38/04* | (2006.01) |
| *B32B 38/16* | (2006.01) |
| *B31B 50/81* | (2017.01) |
| *B31B 100/00* | (2017.01) |

(56) References Cited

U.S. PATENT DOCUMENTS

| | | | | |
|---|---|---|---|---|
| 4,283,011 | A * | 8/1981 | Spector | 239/36 |
| 4,484,768 | A * | 11/1984 | Norfleet | 283/116 |
| 4,529,125 | A * | 7/1985 | Sullivan | A61L 9/12 239/56 |
| 4,858,831 | A | 8/1989 | Spector | |
| 6,460,781 | B1 | 10/2002 | Garcia et al. | A45D 37/00 222/107 |
| 6,688,467 | B2 * | 2/2004 | Krupka et al. | 206/469 |
| 6,736,335 | B2 | 5/2004 | Cuthbert | |
| 6,991,842 | B2 * | 1/2006 | Hurwitz | A47G 27/02 15/215 |
| 6,997,355 | B2 * | 2/2006 | Duquet et al. | 222/209 |
| 7,007,831 | B2 * | 3/2006 | Pennaneac'h et al. | 222/633 |
| 7,815,878 | B1 * | 10/2010 | Wheatley | A63B 43/00 206/315.1 |
| 7,988,073 | B2 * | 8/2011 | Ligny et al. | 239/327 |
| 8,739,973 | B2 * | 6/2014 | Greenland | B65B 3/02 206/232 |
| 2003/0010670 | A1 * | 1/2003 | Dobler | 206/581 |
| 2004/0000599 | A1 * | 1/2004 | Cuthbert | A45D 40/0087 239/327 |
| 2004/0129800 | A1 * | 7/2004 | Duquet | B65D 75/58 239/327 |
| 2009/0266909 | A1 * | 10/2009 | Ligny et al. | A45D 34/02 239/34 |

* cited by examiner

SCENT SAMPLER AND AIR FRESHENER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

It is known in the art to provide small doses of a perfume, cologne or similar fragrance product for sampling by a prospective consumer. The fragrances are sometimes coated onto a paper surface on which an advertisement for the product is printed and included in a magazine or sent in a mailer to consumers. Small amounts of the cologne or perfume can also be provided in bottles or other containers.

In the case of coated paper, the consumer does not have the same experience as spraying the perfume or cologne from a bottle as would be done in normal use. Providing the consumer with a sample in a bottle or other container is relatively expensive.

The present invention overcomes the shortcomings of the prior art in providing an inexpensive device from which a sample of a perfume, cologne, or other product based on a fragrance oil can be sprayed into the air as a mist and sniffed by the consumer to sample the scent in a way similar to using the full product. The invention can also serve as a passive air freshener from which a scent can vaporize into the ambient atmosphere.

SUMMARY OF THE INVENTION

In accordance with a first embodiment of the invention, a die cut cellular foam material is overwrapped with a flexible barrier film which forms an envelope about the cellular foam material. A dosage needle is used to puncture the barrier film and inject the fragrance into the foam material wherein the fragrance is absorbed. The hole created by the needle provides an escape valve for the fragrance oil when pressure is exerted upon the foam material. A card which is foldable upon itself can have an illustration of the scented product on its face.

An adhesive coating or glue is applied to a small area on the inside of the card. The envelope formed by the flexible barrier film, with the cellular foam material containing the fragrance oil inside it, is affixed to the card on the coated adhesive surface. The card can then be folded in half upon itself after adhesive is applied to the inside surfaces of the card whereby the card seals upon itself thereby enclosing the cellular foam material in the flexible barrier film envelope. A hole may be made in an exposed edge of the envelope, or through the card in registration with a hole in the flexible barrier made by the needle.

The consumer can then be provided with a completed sampler which includes a body formed from a card having an illustration of the product. When the user applies pressure to the body, e.g., by squeezing, a mist of the fragrance oil is forced from the cellular foam material through the opening in the flexible barrier film envelope into the atmosphere whereby it can be sampled, i.e., sniffed and evaluated, by the user.

The hole need not be made through the card. In accordance with a second embodiment of the invention, one edge of the sampler can be left open sufficiently to permit the mist to escape from a hole near an edge of the envelope whereby the scent can be released through the open space between the two halves of the card.

In a third embodiment of the invention, a sheet material such as heavy paper or card stock is printed, e.g., with an advertisement for the fragrance product, on one side and covered with a barrier film that is laminated to the opposite side of the sheet material. A heat seal adhesive coating is applied to the exposed surface of the barrier film. Thereafter the sheet material is die cut to form individual cards suitable for use as fragrance samplers. During the die cutting process, each card is perforated to provide one or more openings through which the fragrance scent can escape to the ambient atmosphere, and the card is scored to make a fold line so that it can later be folded onto itself to form an envelope.

A spot of glue is applied to the barrier film about a location on the card that will be in registration with the fragrance escape opening(s) in the card when the card is folded onto itself along the score line.

A wafer of a fragrance fluid retaining foam is applied to the spot of glue on the card and is adhered to the card once the glue has set. The foam is then injected with a fragrance oil which is absorbed into the foam.

Finally, the card is folded onto itself thereby capturing the foam in the envelope thus formed after which the edges of the card are pressed together while heat is applied to activate the heat seal adhesive and form a seal around the border of the envelope through which neither the fragrance oil nor its scent can escape, the only egress for the fragrance scent being through the fragrance escape opening(s) in the card.

In accordance with a fourth embodiment of the invention, the sampler and freshener can be made in a manner similar to that of the third embodiment. However, instead of being made in a continuous in line mode, the device can be fabricated in a sheet form, staged manufacturing process wherein a barrier film is laminated to a sheet of flexible stock, an adhesive coating is applied to film, a spot of another adhesive is applied to film, a foam wafer foam is affixed to the adhesive the adhesive spot, a scented liquid is squirted onto the foam wafer, and the sheet is folded onto itself and sealed by the adhesive coating.

DESCRIPTION OF THE DRAWINGS

Referring now to the drawings.

DESCRIPTION OF THE PREFERRED EMBODIMENTS

Figure 1:
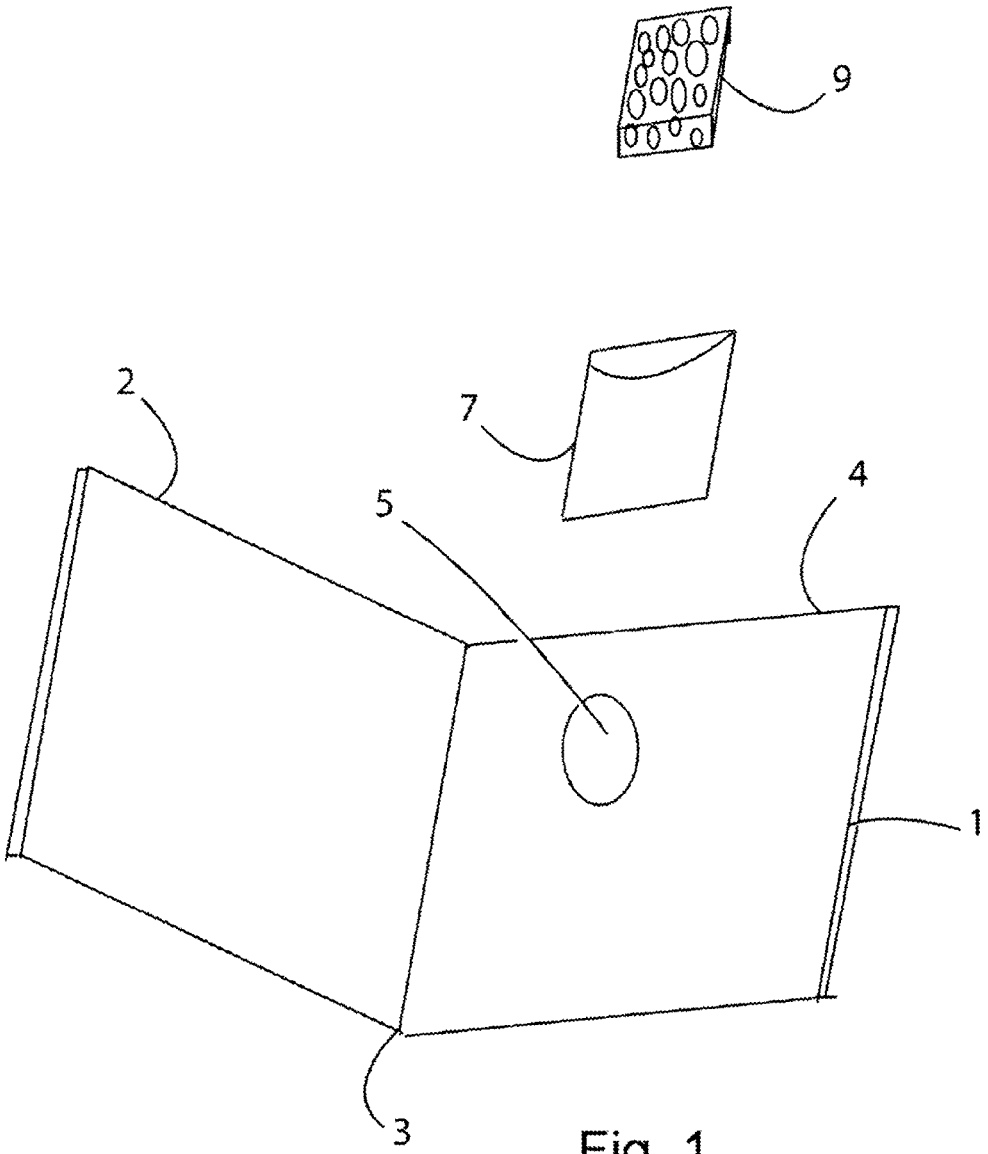
FIG. 1 is an exploded view of the apparatus of a first preferred embodiment of the invention.

Referring now to FIG. 1 of the drawings there is shown an exploded perspective view of the sampler of the invention ready for assembly. A body of the sampler is formed by a rectangular card 1 scored along a vertical line 3 centered on the card 1 so that panels 2 and 4 of the card 1 can readily be folded together. An adhesive material is coated onto the card 1 at a region 5 preferably near the top and inside, i.e., adjacent score line 3 of card 1. A flexible barrier film envelope 7 is provided for receiving a sponge-like wafer 9 die cut from a mass of cellular foam material which, as shown in the drawings, is in the shape of a rectangular solid but may be of virtually any shape. The barrier film material is selected so as not to be degradable by the fragrance oil. Foam material 9 is preferably a poly cellular foam material that will not chemically interact with or be deteriorated by a fragrance oil.

In assembling the scent sampler and air freshener of the invention, foam material 9 is inserted into envelope 7 or, alternatively, wrapped with a barrier film material to form envelope 7 about foam material 9. Once foam material 9 is received within envelope 7, envelope 7 is hermitically sealed to prevent unwanted communication between the ambient atmosphere and the vapors emitted from the fragrance oil absorbed into the cellular foam material within envelope 7.

Figure 2:
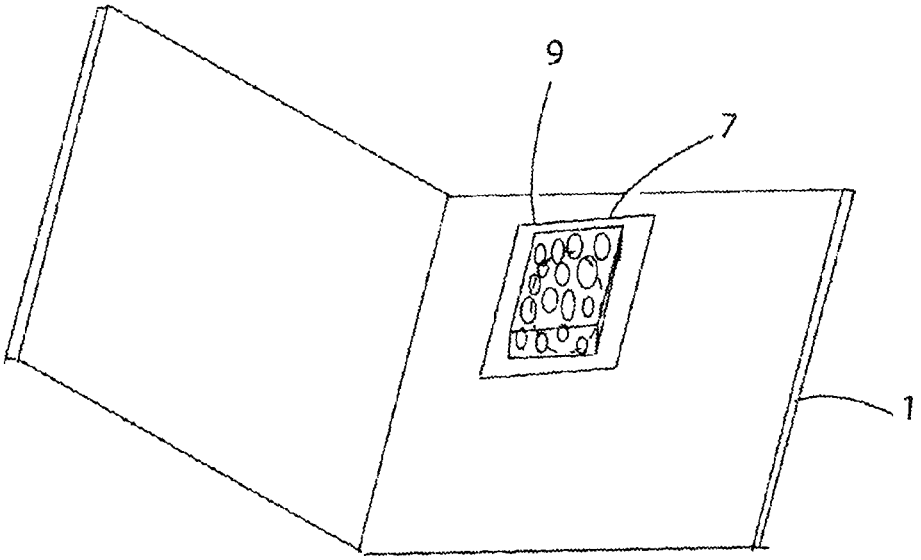
FIG. 2 is a perspective view of the apparatus of FIG. 1 in an intermediate stage of assembly.

Referring now to FIG. 2 of the drawings, envelope 7 containing foam material 9 is affixed to the card 1 by placing envelope 7 over the adhesive spot 5 and exerting mild pressure to attach envelope 7 to the card 1 with foam material 9 sealed therein.

Foam material 9 may then be injected with a fragrance oil by inserting the needle of a syringe or other filling device (not shown) through the barrier film material 7 into foam material 9. As the fragrance oil is injected into foam material 9 it is absorbed and stored therein.

In the first preferred embodiment of the invention, the needle is inserted into foam material 9 through the top of envelope 7 which is left exposed to the outside air after the card 1 is sealed upon itself by folding panel 2 over panel 4 and sealing them together.

Figure 3:
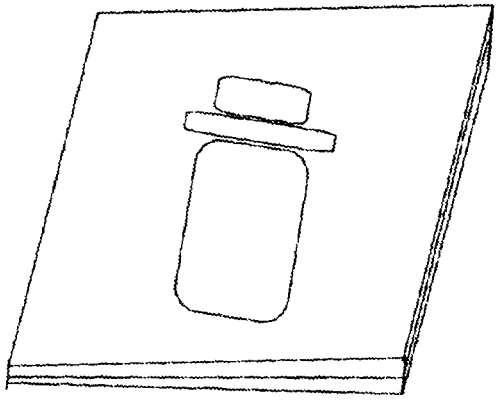
FIG. 3 is a perspective view of the apparatus of FIG. 1 after assembly has been completed.

When panel 2 of card 1 is folded onto panel 4 of card 1, envelope 7, containing foam material 9, which has been affixed to the adhesive spot 5, is sandwiched between panels 2 and 4 to form the fragrance sampler shown in FIG. 3.

As can be seen in FIG. 3, the outer face of panel 2 may be imprinted with a graphic image or other advertising copy to identify and promote the scent product which is based on the fragrance oil contained in foam material 9.

After panels 2 and 4 are folded together, they may be secured to one another by a glue or other adhesive material coated onto inner surface(s) of one or both of panels 2 and 4. Selecting an adhesive which will not chemically interact with barrier film material 7 permits the inner surface of panel 4 and the exposed exterior surface of envelope 7 to be coated with adhesive material, as may be the inside surface of panel 2. A contact cement can be coated onto the upward (inner) facing surfaces of panels 2 and 4 to provided instant sealing once panel 2 is folded onto panel 4. A heat seal coating may also be applied to one or both panels 2, 4 of card 1 for sealing panels 2 and 4 together upon application of heat under pressure.

It will be appreciated that other fastening techniques may be used to secure panel 2 and panel 4 together such as stapling, tacking, sewing, riveting, or any other conventional fastening technique for attaching two surfaces of a card stock together.

Figure 4:
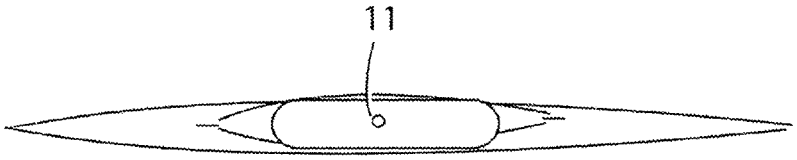
FIG. 4 is a top plan view of the apparatus of FIG. 1.
Figure 5:
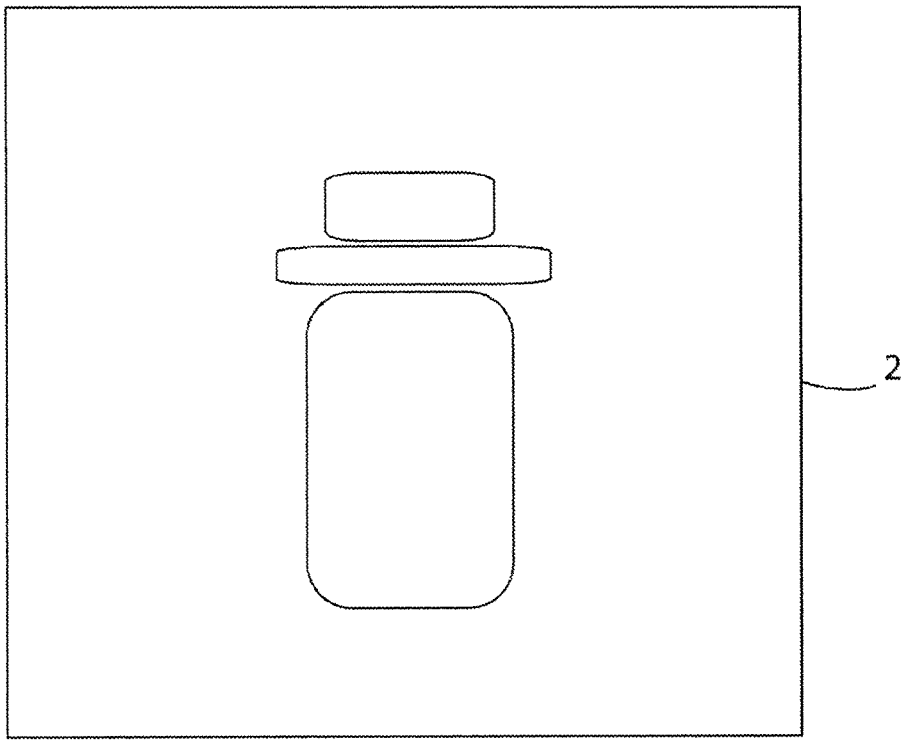
FIG. 5 is an elevation view of the apparatus of FIG. 1.
Figure 6:
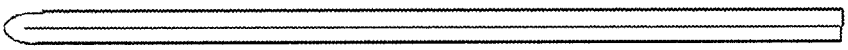
FIG. 6 is a bottom plan view of the apparatus of FIG. 1.

As can be seen in FIG. 4 of the drawings, the needle hole 11 is made at the top of envelope 7 for permitting the fragrance oil scent to be released to the atmosphere for sampling by a user.

In use, a consumer can squeeze the sampler by pressing panel 2 toward panel 4 thereby exerting pressure on foam material 9 through envelope 7. The pressure increase inside envelope 7 causes a mist of the fragrance oil stored in foam material 9 to escape through the opening 11 whereby it can be sniffed by the consumer.

Figure 7:
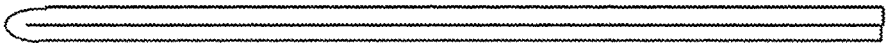
FIG. 7 is a top plan view of a second embodiment of the invention.
Figure 8:
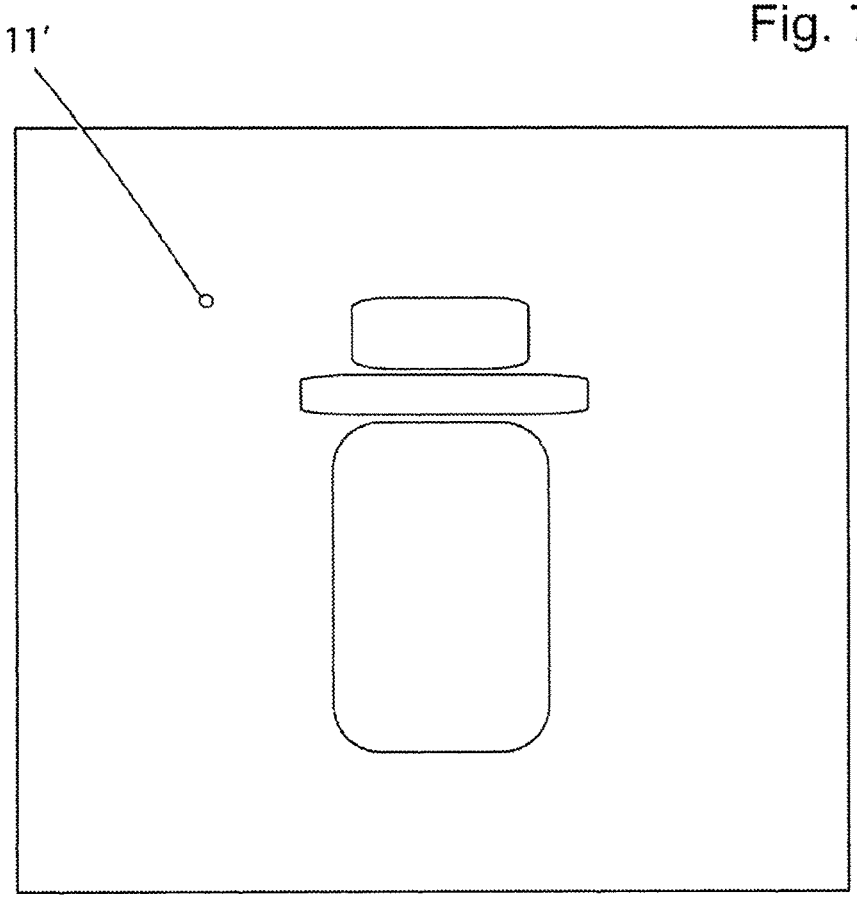
FIG. 8 is an elevation view of the second embodiment shown in FIG. 7.

Referring to FIG. 7 of the drawings, there is shown a second embodiment of the invention wherein, instead of inserting the needle through the top of envelope 7, an opening 11' is made through the outer surface of panel 2 of the card 1. Another opening can be made within the surface of envelope 7 before panels 2 and 4 are sealed together. When envelope 7 is affixed to the adhesive spot 5, it is placed in position so that when panel 2 is folded over envelope 7 onto panel 4, the holes in panel 2 and envelope 7 are in registration.

Figure 9:
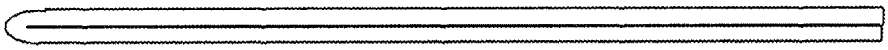
FIG. 9 is a bottom plan view of the second embodiment shown in FIG. 7.

With the foregoing construction, all edges of panels 2 and 4 can be sealed together to form a sampler fully closed at the top, as can be seen in FIG. 7, and bottom, as can be seen in FIG. 9. When the consumer squeezes panels 2, 4 together, vapor from the fragrance oil is released through the registered openings in envelope 7 and panel 2 and into the ambient environment where it can be sniffed.

Instead of separately puncturing envelope 7 and panel 2, which requires that envelope 7 be assembled in precision alignment with panel 4 of card 1 so that the respective holes in panel 2 and envelope 7 are in registration, the aperture 11' can be made after the sampler is fully assembled. That is, envelope 7 containing foam material 9 can be adhered to the adhesive spot 5 after which panel 2 is folded onto panel 4 and all edges are sealed. Thereafter, a needle strong enough to penetrate card 1 can be inserted through the face of panel 2 and, through envelope 7, into foam material 9 after which the fragrance oil can be injected and absorbed into foam material 9.

It is preferred that care be taken so that the puncture needle does not penetrate the underside of envelope 7 at its interface with panel 4 of card 1 as this would cause the fragrance material to exit from the rear side of the sampler.

Although it has been found that the embodiments of FIGS. 1-9 of the drawings perform their function admirably, the following variation of the invention dispenses with the need for encapsulating the scent-containing foam material in a barrier film envelope to prevent loss of the fragrance oil and resulting contamination.

Figure 10:
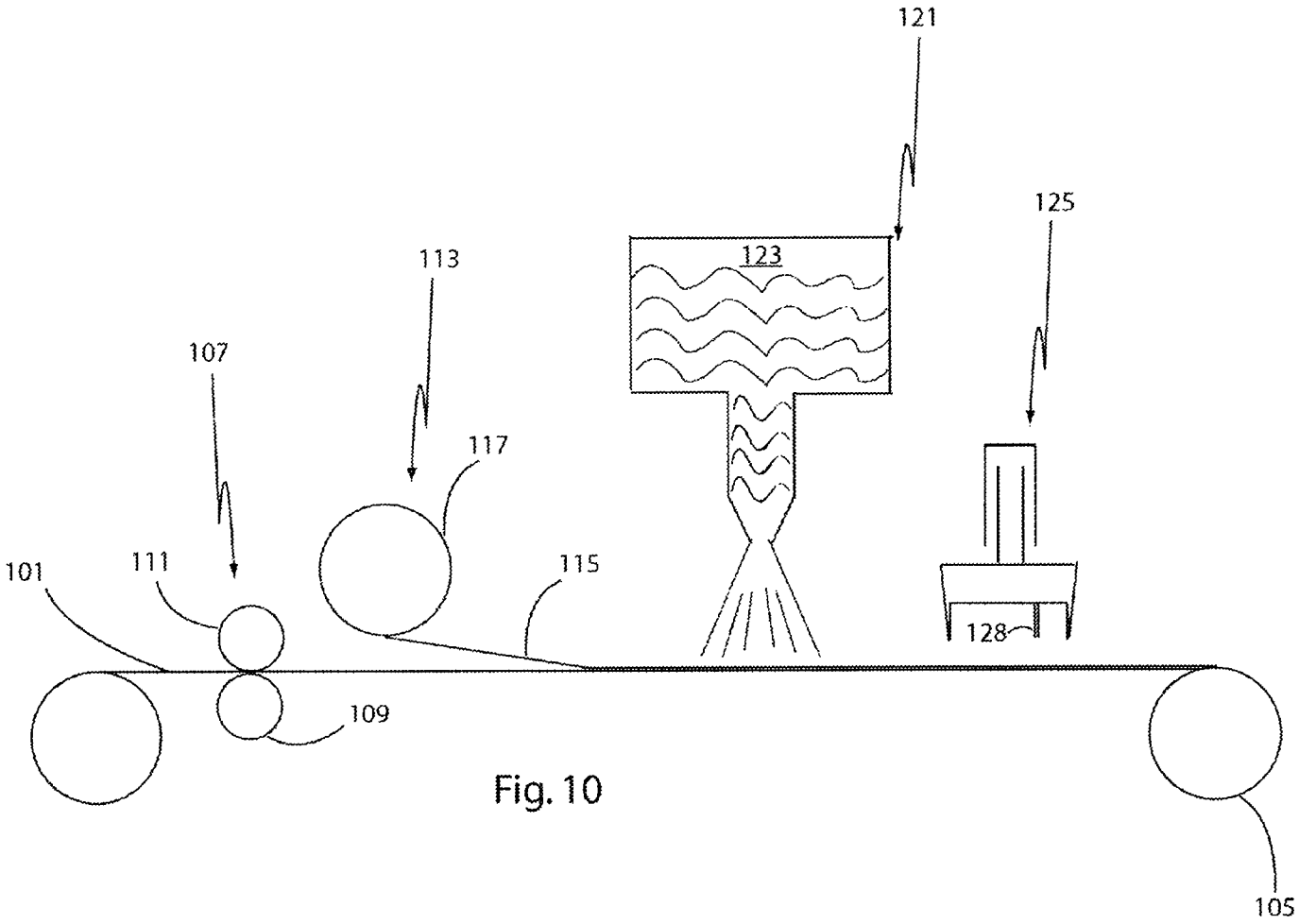
FIG. 10 is a schematic view of a third embodiment of the invention during an initial stage of manufacture.

Referring now to FIG. 10, there is shown a web of sheet material 101 dispensed from a supply spool 103 driven to move toward a take-up spool 105. The sheet material 101 is preferably a flexible card stock, but can be paper, or even a flexible plastic material, textile fabric, metallic foil, or other flexible sheet material.

The sheet material 101 is passed through a printing station 107 have a print roller 109 and support roller 111 for printing the underside of the sheet material, preferably with a promotional product illustration, name, and/or message.

At a subsequent station, 113, a barrier film 115 is applied from a spool 117 to the top, unprinted side of the sheet material 101. An adhesive material (not shown) is applied between the barrier film 115 and sheet material 101 to laminate the barrier film 115 to the sheet material 101 thereby forming a unitary web 119.

The barrier film 115 should be impervious to the fragrance oil from which the scent is to be sampled. The barrier film is, therefore, preferably a polyester film or polypropylene film, both polyester and polypropylene having been found to exhibit the necessary properties for retaining fragrance oil and the scent it emits and preventing the oil from directly contacting the sheet material 101.

The adhesive for fixing the barrier film 115 to the sheet material 101 can be a liquid adhesive or a pressure sensitive one. The barrier film 115 may have the adhesive applied to the surface to be mated with the sheet material 101 before the sheet material 101 is printed, as well as after.

After the film 115 is applied to the sheet material 101, the unitary web 119 is passed through a station 121 whereat a heat seal coating material 123 is applied to the exposed surface of the film 115. The heat seal coating material 123 may cover the entire surface of the film 115 or only a margin along the perimeter of cards to be die cut from the unitary web 119 at a subsequent station 125. The heat seal material 123 is preferably a water based material which can be sprayed onto the film 115 and then dried to leave a heat seal coating. The selection of a suitable water based heat sealing material will be known to those skilled in the art.

Following application of the heat seal coating material 123 to the film 115, the web of sheet material 101 is passed through a die cutting station 125. There, identical cards are sequentially cut from the web of sheet material 101 in a size an shape consistent with the desired dimensions and shape of an envelope for the scent sampler and air freshener. The repeat of the graphics printed on the underside of the sheet material 101 is preferably synchronized to the size and spacing of the cards to be die cut to provide each finished sampler and freshener with an image identical to the image of all other samplers from the same run.

At the die cutting station 125, a fold line is scored into the unitary web 119 dividing each card into two panels 131, 133 in order to enable each card cut from the web 119 to be folded upon itself. Where the fold line is selected to be coincident with the centerline of the card, the edges of the respective panels can be joined in registration.

A further operation that takes places during the die cutting process is the perforation of each card cut from, or to be cut from, the unitary web 119 with one or more small openings through which the scent of the fragrance oil to be sampled or dispersed can pass.

Figure 11:
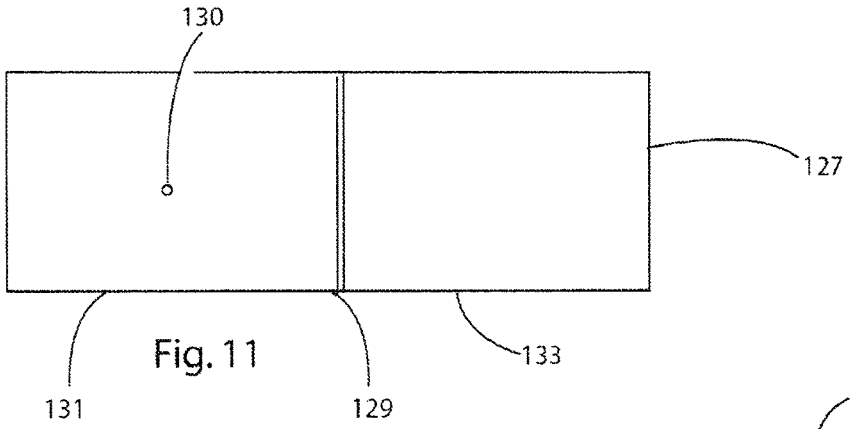
FIG. 11 is a plan view of the third embodiment of the invention after completing the stage of manufacture illustrated in FIG. 10.

Referring now to FIG. 11 of the drawings, there is shown a card 127 which has been die cut from the unitary web 119. The centerline 129 of card 127 has been scored during die cutting of the card 127, thereby dividing the card 127 into two congruent panels 131 and 133, and an opening 130 distal from a circumference of the first panel has been made by perforating the panel 131, of the card 127, during die cutting of the card 127 with a punch 128 at the cutter station 125. Although only a single opening 130, for passing the fragrance scent to the ambient environment, is shown in the drawings, two or more such openings can be made in the panel 131 during die cutting of each card 127. Also, the fold line need not be coincident with the centerline, e.g. where it may be desirable to have incongruent panels.

Figure 12:
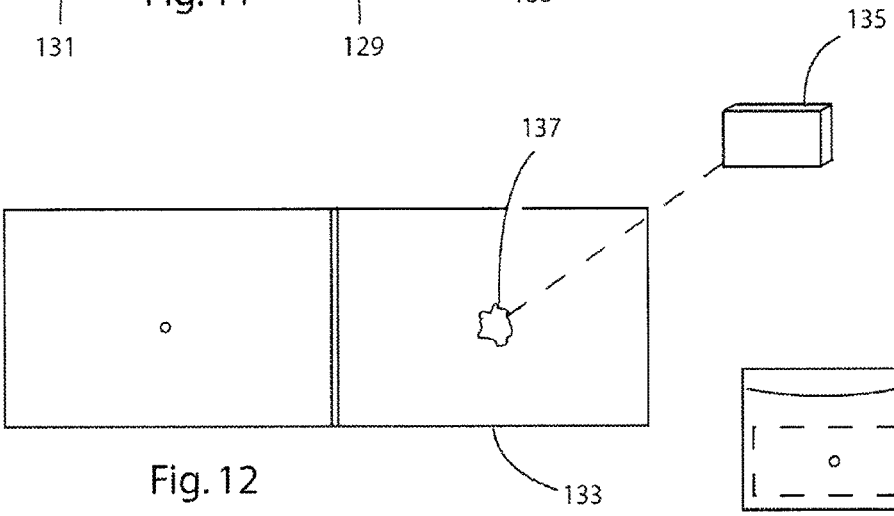
FIG. 12 is a partial plan, partial perspective exploded view of the third embodiment of the invention during still a further stage of manufacture.
Figure 12A:
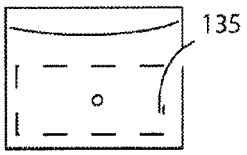
FIG. 12A is a plan view of an optional environment for an element shown in FIG. 12.

Turning now to FIG. 12, there is shown a wafer of a spongy foam material 135 which has been formed in the shape of a solid rectangle the largest face of which has a length and width less than the respective length and width of each of the panels 131, 133 so that it may be attached to the film surface of the card 127 within the circumference of the one of the panels, e.g., panel 133. Optionally, the attached wafer 135 may be disposed within an interior envelope formed from a flexible barrier film and having an aperture which, when in registration with the first panel opening, permits scented vapor to escape through the aperture in the interior envelope and through the first panel opening to the ambient atmosphere as shown in FIG. 12A.

The foam from which the wafer 135 is made is preferably an open cell polyester hydrophylic foam. This foam has been found to have excellent retention properties with respect to fragrance oils whereby it is not necessary to enclose the wafer of foam in an envelope formed from a barrier film as in the first and second embodiments of the invention. Leakage from the polyester hydrophylic foam wafer 135, when not over-saturated, has been found to be minimal and the film laminate 115 of the card 127 is a barrier to contact between a fragrance oil to be absorbed into the polyester hydrophylic foam wafer 135 and the card stock to which the film 115 is laminated.

In order to secure the foam wafer 135 to the panel 133, a dab of glue 137 is applied to the panel 133 at an area surrounding the reflection about the centerline 129 of the opening 135 in the panel 133. This may be accomplished by applying the glue 137 to the second panel at an area surrounding the reflection about the fold line of the opening in the first panel.

Figure 13:
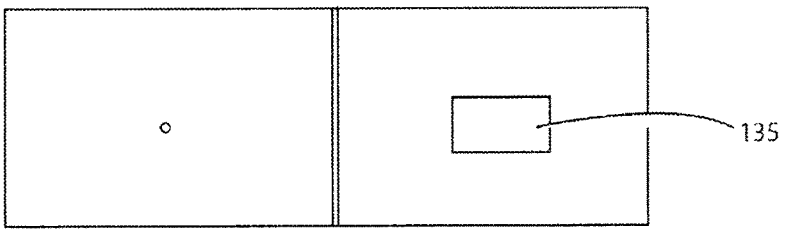
FIG. 13 is a plan view of the third embodiment of the invention following completion of the further stage of manufacture illustrated in FIG. 12.

The glue 137 may be a hot melt glue or a cold setting glue. This positioning will enable the opening 130 to overlie the foam wafer 135 when the panel 131 of card 127 is folded onto adjacent panel 133, i.e., when the card is folded onto itself. Thereafter, as shown in FIGS. 12 and 13, the foam wafer 135 is pressed onto the glue 137 which is allowed to set for affixing the foam wafer 135 to the film laminated surface of the panel 133.

Figure 14:
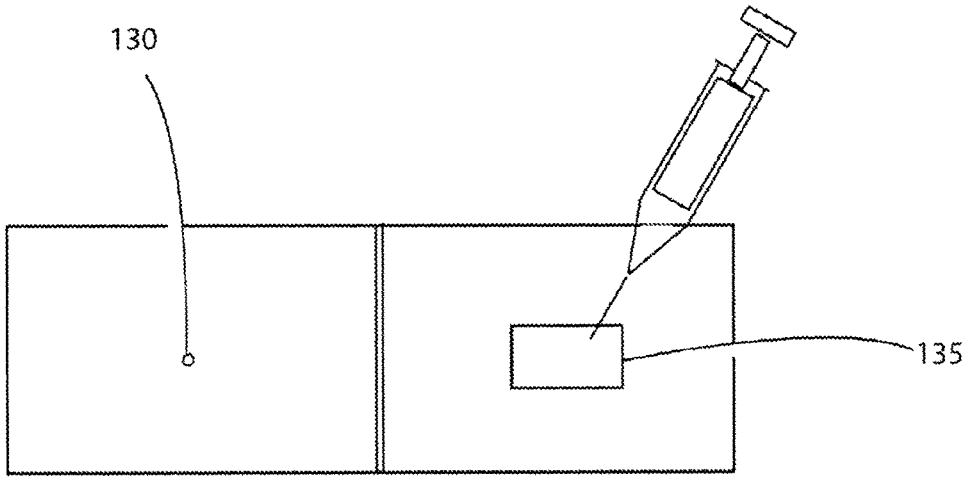
FIG. 14 is a partial plan, partial perspective view illustrating a still further step in the manufacture of the third embodiment of the invention.

Referring now to FIG. 14, infusion of the fragrance oil into the foam wafer 135 takes place by injecting into the foam wafer 135, or spraying or squirting onto the foam wafer 135, a quantity of the fragrance oil sufficient to emit a generous amount of scent but not large enough to oversaturate the foam wafer 135 which absorbs the fragrance oil during injection, spraying or squirting.

Figure 15:
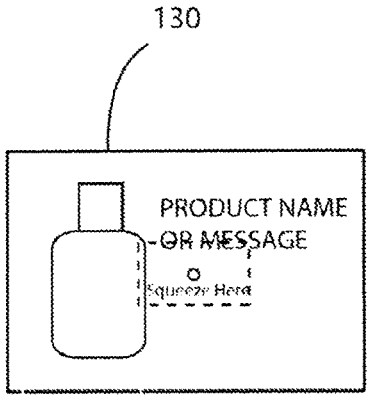
FIG. 15 is a plan view of the third embodiment at a still later stage of manufacture.
Figure 16:
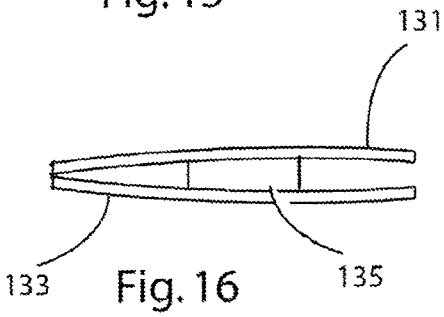
FIG. 16 is a top view of the third embodiment shown in FIG. 15, the bottom view being substantially identical thereto.
Figure 17:
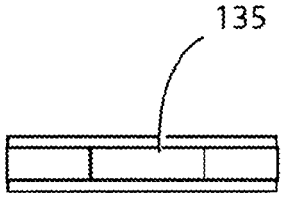
FIG. 17 is a right end view of the third embodiment shown in FIG. 15.

Thereafter, the card 127 is folded about the scored fold line 129 so that the opening 130 overlies the foam material 135 and the printed side of each panel 131, 133 is exposed for viewing as can be seen in FIG. 15. As can be seen in FIGS. 16 and 17, at this time the thickness of the resilient foam wafer 135 urges the panels 131 and 133 apart so that they are joined only along the scored fold line 129 about which they have been folded, one onto the other.

Figure 18:
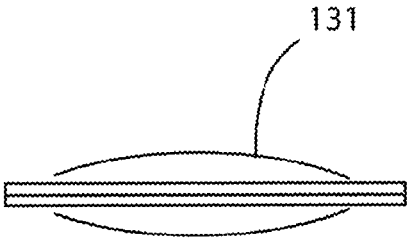
FIG. 18 is a top view of the completed third embodiment of the invention, the bottom view being substantially identical thereto.
Figure 19:
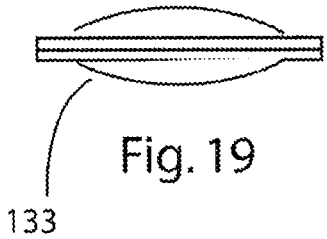
FIG. 19 is a right end view of the third embodiment of the invention shown in FIG. 18.
Figure 20:
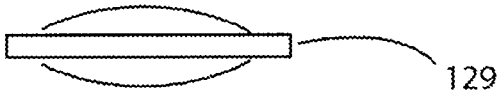
FIG. 20 is a left end view of the third embodiment of the invention shown in FIG. 18.

Finally, the panels 131 and 133 are secured together along their edges by applying heat and pressure to urge the edges together whereby the heat seal adhesive coating on the mutually facing surfaces panels 131 and 133, i.e., that has been applied to the exposed surface of the barrier film laminate 115, fuses the edges of the panels together to form a hermetic seal as shown in FIGS. 18-20. The panels thereby become the front and back panels of a fully sealed envelope having an interior chamber in which the foam wafer 135 which has been infused with the fragrance oil is encapsulated.

Vapor containing the scent to be sampled will then be emitted by the fragrance oil that has been absorbed into the foam wafer 135 from inside the envelope to the outside ambient air through the only available exit, that is, the opening 130 in panel 131.

For sampling the scent, e.g., by sniffing, the rate of emission of scented vapor through the opening 130 can be increased by applying pressure to the front face of the envelope, preferably at a point overlying the foam wafer 135 and proximate the opening 130 thereby compressing the wafer and releasing a mist of the fragrance oil through the opening 130.

Figure 21:
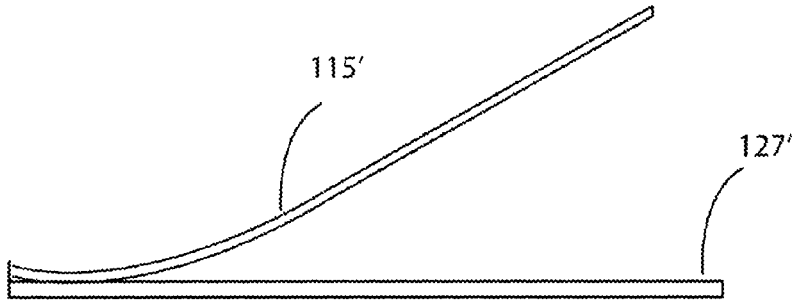
FIG. 21 is a schematic view of a fourth embodiment during an initial stage of manufacture.
Figure 22:
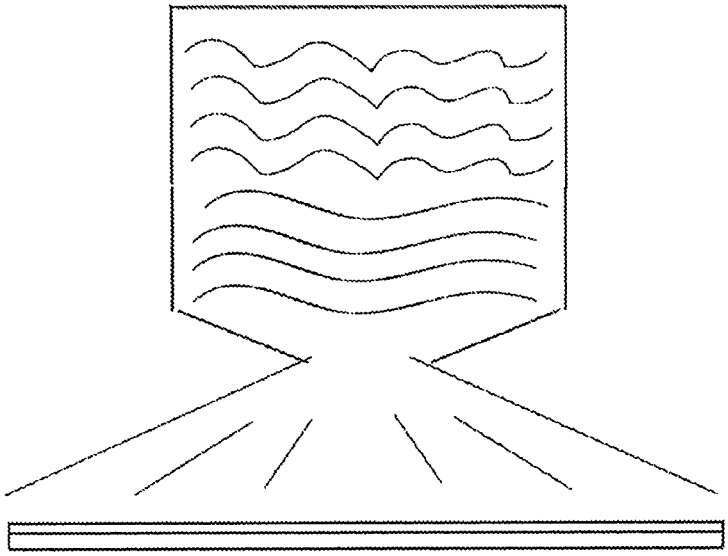
FIG. 22 is a schematic view of the fourth embodiment during a further stage of manufacture.
Figure 23:
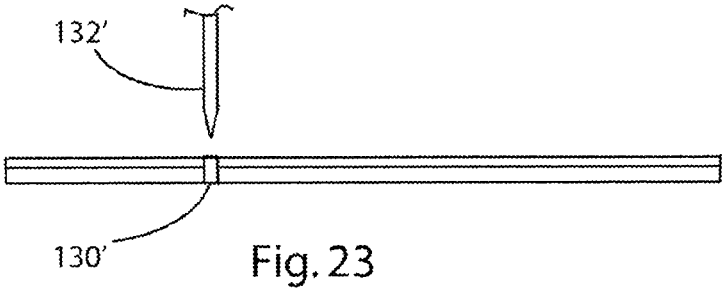
FIG. 23 is a schematic view of the fourth embodiment during still a further stage of manufacture.
Figure 24:
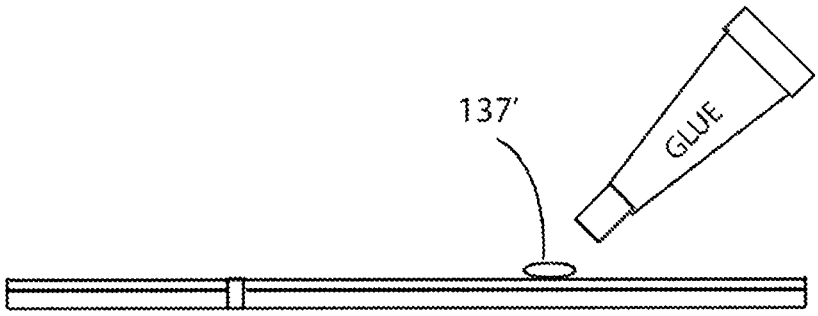
FIG. 24 is a schematic view of a fourth embodiment during still a further stage of manufacture.
Figure 25:
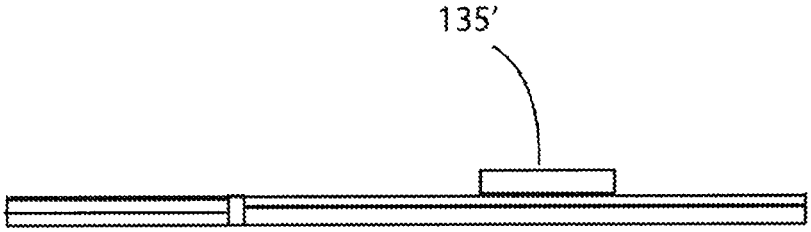
FIG. 25 is a schematic view of the fourth embodiment during still a further stage of manufacture.
Figure 26:
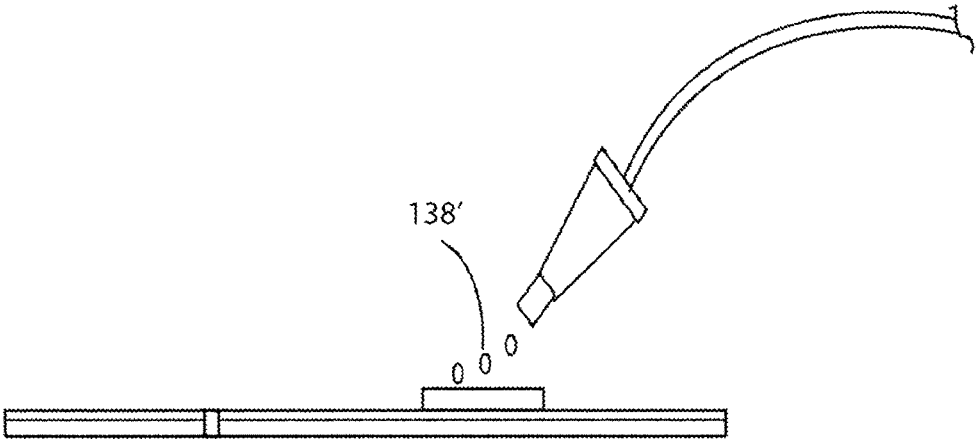
FIG. 26 is a schematic view of the fourth embodiment during still a further stage of manufacture.
Figure 27:
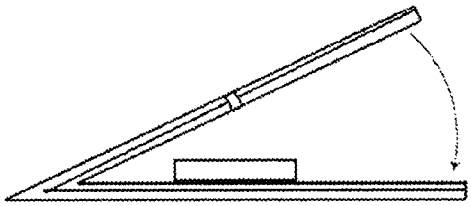
FIG. 27 is a schematic view of the fourth embodiment during still a further stage of manufacture.

Referring to FIGS. 21-27, the sampler and freshener can be made in a manner similar to that of the third embodiment. However, instead of being made in a continuous in line mode, the device can be fabricated in a sheet form, staged manufacturing process wherein a barrier film 115' is laminated to a sheet of flexible stock 127' as shown in FIG. 21, an adhesive coating is applied to film 115' as shown in FIG. 22, a hole 130' is made in the film and stock laminate *by a needle 132'* as shown in FIG. 23, a spot of another adhesive 137' is applied to film 115' as shown in FIG. 24, a foam wafer 135' is affixed to the adhesive spot as shown in FIG. 25, a scented liquid is squirted onto the foam wafer 138' as shown in FIG. 26, and the sheet is folded onto itself and sealed by the adhesive coating as shown in FIG. 27.

For use as a sampler, the construction of the invention may be included in a point of sale display for actuation by prospective customers for perfume, toilet water, cologne or the like. Alternatively, the sampler can be distributed to consumers at a point of sale, by mail or other means of delivery, or as an insert in magazines, brochures or other publications.

In addition to use of the invention for sampling fragrances, it may be left as an unattended air freshener in a place desired to be freshened by the aroma of the scent, e.g., in a closet, a furniture drawer or an item of luggage. Depending on the nature and concentration of the scent, the invention can also serve as a visually pleasing room deodorizer.

It is to be appreciated that the foregoing specification describes three embodiments of an apparatus and method for its manufacture to which variations and modifications may be made without departing from the spirit and scope of the invention.

For example, the card 1, 127 need not be rectangular but can have any shape, preferably one which is aesthetically pleasing. The body of the sampler can be formed from materials other than card stock, including plastic, fabric, or any other flexible material that can be deformed to exert pressure on an absorbent resilient wafer for releasing a scent from a fragrance oil or other liquid carrier. One or more additional openings may be formed, not only in the front panel of the sampler, but in the rear panel as well.

Although the preferred embodiments of the invention are formed from a single card having adjacent panels folded one over the other, two separated panels can be stacked and sealed together about their entire circumferences.

What is claimed is:

1. A scent sampler and air freshener comprising a first [flexible] panel formed from a sheet material and having an outer surface, an inner surface opposite said outer surface, and an opening distal from a circumference of said first panel extending through said first panel between said inner surface and said outer surface, a second [flexible] panel formed from a sheet material and having an outer surface and an inner surface opposite said outer surface, said first and second [flexible] panels being affixed together about their respective circumferences to form an envelope with an interior region whereat said first [flexible] panel and said second [flexible] panel are mutually separable for defining a chamber therein, said opening being in communication with said chamber, a scent emitting liquid, a wafer of compressible, resilient, absorbent material disposed within said chamber and infused with a quantity of said scent emitting liquid, *said wafer being spaced from said affixed together outer circumferences of said first panel and said second panel,* said opening being in registration with an area of, and overlying, said wafer of compressible, resilient, absorbent material so that upon application of pressure to [the] *a* front face of said envelope, said *panel with said* opening is brought into contact with said wafer and said wafer is compressed releasing a [mist of] scented vapor through said opening to the ambient atmosphere, and said resilient wafer urges said first [flexible] panel and said second [flexible] panel apart.

2. A scent sampler and air freshener in accordance with claim 1 wherein said first panel and said second panel are two adjacent panels of a single piece of sheet material, and said first panel is folded over said second panel.

3. A scent sampler and air freshener in accordance with claim 1 further comprising an interior envelope formed from a flexible barrier film disposed within said chamber, said wafer of compressible absorbent material being disposed within said interior envelope, said envelope having an aperture in registration with said first panel opening for permitting said scented vapor to escape through said aperture in said interior envelope and through said first panel opening to the ambient atmosphere.

4. A scent sampler and air freshener in accordance with claim 1 wherein said wafer comprises a resilient spongy material.

5. A scent sampler and air freshener in accordance with claim 4 wherein said wafer comprises a foam material.

6. A scent sampler and air freshener in accordance with claim 5 wherein said foam material comprises an open cell hydrophylic foam.

7. A scent sampler and air freshener in accordance with claim 6 wherein said open cell hydrophylic foam comprises polyester.

8. A scent sampler and air freshener in accordance with claim 1 wherein at least one of said first panel and second panel comprises a barrier film laminate affixed to [its] *a* first surface *thereof* to protect said sheet material from leakage of said liquid out of said wafer.

9. A scent sampler and air freshener in accordance with claim 8 wherein said barrier film laminate comprises polyester.

10. A scent sampler and air freshener in accordance with claim 1 wherein said outer surface of said first panel is imprinted with text and/or graphics.

11. A scent sampler and air freshener in accordance with claim 1 wherein said wafer is affixed to at least one of said first panel inner surface and said second panel inner surface.

12. A scent sampler and air freshener in accordance with claim 1 wherein an area of said inner surface of said first panel and an area of said inner surface of said second panel are coated with a heat seal adhesive for sealing said first panel to said second panel.

13. A scent sampler and air freshener in accordance with claim 1 wherein said wafer releases a scented mist of said liquid through said opening in response to compression of said wafer by pressing said first panel and second panel towards one another in an area overlying said chamber.

14. A scent sampler and air freshener in accordance with claim 1 wherein said wafer is glued to an area of said inner surface of said second panel within said chamber.

* * * * *